United States Patent
Chong et al.

(10) Patent No.: US 7,875,008 B2
(45) Date of Patent: Jan. 25, 2011

(54) BARRIER CATHETER APPARATUS AND METHOD

(75) Inventors: Colin Chong, Glendale, CA (US); Keith Oberg, Valencia, CA (US); Paul Mounce, Burbank, CA (US); Peter C. Lord, Valencia, CA (US); William P. Van Antwerp, Valencia, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1917 days.

(21) Appl. No.: 10/924,519

(22) Filed: Aug. 23, 2004

(65) Prior Publication Data

US 2005/0021001 A1 Jan. 27, 2005

Related U.S. Application Data

(62) Division of application No. 10/036,081, filed on Dec. 28, 2001, now abandoned.

(60) Provisional application No. 60/317,358, filed on Sep. 5, 2001.

(51) Int. Cl.
*A61M 5/00* (2006.01)
*A61M 25/18* (2006.01)

(52) U.S. Cl. .................. 604/247; 604/264; 604/537

(58) Field of Classification Search .............. 604/30, 604/34, 95.02, 239, 264, 266, 65–67, 246, 604/247, 288.01–288.04, 535, 533, 537
See application file for complete search history.

(56) References Cited

U.S. PATENT DOCUMENTS

| | | | |
|---|---|---|---|
| 4,284,081 A * | 8/1981 | Kasper et al. | 604/102.02 |
| 4,340,615 A | 7/1982 | Goodwin et al. | |
| 4,921,483 A | 5/1990 | Wijay et al. | |
| 4,966,579 A | 10/1990 | Polaschegg | |
| 5,195,960 A * | 3/1993 | Hossain et al. | 604/34 |
| 5,916,192 A | 6/1999 | Nita et al. | |
| 6,004,310 A | 12/1999 | Bardsley et al. | |
| 6,010,521 A | 1/2000 | Lee et al. | |
| 6,096,012 A | 8/2000 | Bogert et al. | |
| 6,358,238 B1 | 3/2002 | Sherry | |
| 6,663,606 B1 | 12/2003 | Barry et al. | |
| 2002/0010416 A1 * | 1/2002 | Uflacker | 604/35 |

OTHER PUBLICATIONS

Office Action dated Apr. 24, 2003 from related U.S. Appl. No. 10/036,081.
Office Action dated Sep. 24, 2003 from related U.S. Appl. No. 10/036,081.

(Continued)

*Primary Examiner*—Kevin C Sirmons
*Assistant Examiner*—Catherine N Witczak
(74) *Attorney, Agent, or Firm*—Foley & Lardner LLP

(57) ABSTRACT

A catheter for use in delivery or withdrawal of a formulation, wherein the catheter has an outer layer comprising a biocompatible material and a barrier layer comprising a material that provides a more effective barrier than the outer layer against inward and outward diffusion of substances that may cause destabilization of the formulation. The catheter may include a flared distal end tip to aid in the release, during a bolus delivery or catheter flush, of any obstruction situated at the distal end tip of the catheter. The catheter may also include a slit valve at the distal end tip which has one or more and, preferably a plurality of slits that may be elastically extended to an open position by the expulsion of the formulation during an IIP pump stroke. During the interval between IIP pump strokes, the slits return to a closed position and hinder the inflow of body fluid into the distal end tip.

21 Claims, 7 Drawing Sheets

OTHER PUBLICATIONS

Office Action dated Jun. 18, 2004 from related U.S. Appl. No. 10/036,081.
Office Action dated Dec. 15, 2004 from related U.S. Appl. No. 10/036,081.
Office Action dated Jun. 2, 2005 from related U.S. Appl. No. 10/036,081.
PCT International Search Report as issued in International Application No. PCT/US02/28173, Mailing date Mar. 11, 2003.

* cited by examiner

BARRIER CATHETER APPARATUS AND METHOD

CROSS-REFERENCE TO RELATED APPLICATIONS

This application is a divisional of application Ser. No. 10/036,081 filed Dec. 28, 2001, which is in turn claims the benefit of prior filed U.S. Provisional Application Ser. No. 60/317,358, filed Sep. 5, 2001 and relate to co-pending U.S. patent application Ser. No. 10/035,831, filed Dec. 28, 2001. The entirety of each which are incorporated herein by reference.

BACKGROUND OF THE INVENTION

1. Field of the Invention

The present invention relates, generally, to improvements in catheters, and, in preferred embodiments, to a catheter that significantly reduces diffusion of substances through the catheter wall and, in further preferred embodiments, possibly hinders the formation of obstructions in the distal end tip of the catheter.

2. Description of Related Art

In the medical arts, catheters are used to inject fluids into or drain fluids away from the body. Catheters may be used in combination with a device such as a pump, which is implanted in the body of a patient, the pump being suitable for the programmed delivery of measured doses of a formulation. (A formulation is defined in the present disclosure as the substance being conveyed by the catheter. This substance may comprise either a mixture of different components or it may be a single, pure substance.) A typical example of such use is the intraperitoneal delivery of an insulin formulation. FIG. 1 illustrates an example of this use. As shown in FIG. 1, an implantable infusion pump (IIP) 10 is implanted in a patient below the skin and above the muscle in the abdomen. The IIP 10 will then dispense an infusion formulation (such as an insulin formulation) through the peritoneum wall 12 via a catheter 14. A lead 16 may connect IIP 10 to a sensing device (not shown) that is used to regulate the delivery of the infusion formulation.

Depending on the circumstances, it may be necessary or desirable that the IIP and catheter remain within the patient for extended time periods ranging from a number of days to a number of years. Thus, the catheter is exposed to the body fluids of the patient. Substances within these body fluids can, over time, diffuse through the catheter wall and interact with the infusion formulation within the lumen of the catheter. The diffusion of certain molecules may lead to the formation of catheter obstructions. For example, it is believed that diffusion of one or more molecules (for example, of $CO_2$ and/or phenol) through the wall of a catheter carrying an insulin formulation may lead to precipitation and eventually to the formation of deposits that may result in catheter obstructions. In addition, obstructions often form at the distal end tip of the catheter, possibly as a result of $CO_2$ mixing with the infusion formulation that is present near the tip, especially during the interval between pump strokes of the IIP.

An additional problem with inward diffusion of molecules through the wall of a catheter is that the molecules interact with the infusion formulation. Thus, the composition of the infusion formulation within the catheter may be destabilized. This makes it difficult to accurately control the properties, composition, and/or stability of the infusion formulation delivered to the infusion site. Along with the problem of diffusion of molecules through the wall into the catheter is the related problem of outward diffusion of molecules of the infusion formulation components through the wall of the catheter and into the patient at other than the infusion site. For example, when an insulin formulation is being conveyed by a catheter, preservatives within the insulin formulation, such as phenol and m-cresol, may diffuse out of the catheter. Again, as a result of this outward diffusion, the properties, composition, and/or stability of the infusion formulation delivered to the infusion site will be difficult to control. Furthermore, it is believed that the diffusion of phenol from the insulin formulation destabilizes the insulin formulation and has a tendency to precipitate and lead to the formation of catheter obstructions.

As the technology improves, implant devices such as the IIP are becoming smaller. Because of the smaller size of the IIP, only a smaller volume of the infusion formulation can be accommodated within the IIP. Thus, higher concentration infusion formulations are normally used. With higher concentration infusion formulations, it is even more important that the properties, composition, and/or stability of the infusion formulation are accurately controlled.

An exemplary catheter comprises a lumen which extends through an inner wall of polyethylene and a relatively flexible outer wall of bio-compatible polymer material such as silicone rubber. The lumen is the medium through which the infusion formulation will pass. The distal end of the catheter is usually located at an infusion site. The proximal end of the catheter is usually attached to a source of the infusion formulation, which may be within an IIP.

An exemplary catheter, as discussed above, may comprise an inner wall of polyethylene and an outer wall of silicone rubber. Both of these materials can be insufficient barriers to diffusion. In addition, the exemplary catheter discussed above allows a infusion formulation to be resident in the catheter for long periods of time before it is dispensed from the distal end. $CO_2$ and other substances present in body fluids may diffuse and/or mix with the infusion formulation in the distal end tip and cause obstructions to form.

Accordingly, there is a demand for a catheter that restricts diffusion into or out of the catheter walls. There is also a demand for a catheter that will reduce the chances that the infusion formulation flowing through the lumen will be hindered by obstructions in the distal end tip of the catheter.

SUMMARY OF THE INVENTION

Therefore, it is an advantage of embodiments of the present invention to provide a catheter which provides a significant barrier to diffusion of $CO_2$ and other substances into the lumen of the catheter.

It is a further advantage of embodiments of the present invention to provide a catheter that inhibits diffusion of preservatives and other substances within an infusion formulation outward through the walls of the catheter and into the body of the patient before reaching the distal end of the catheter.

It is a further advantage of embodiments of the present invention to provide a catheter which inhibits deposit formation that can tend to occur at or near the distal end tip and facilitates the expulsion during delivery, for example, delivery of a bolus or catheter flush.

These and other advantages are accomplished according to a catheter which provides a significant barrier to inward diffusion of any undesirable substance into the lumen of the catheter and/or to outward diffusion of any infusion formulation contained within the lumen of the catheter.

In a preferred embodiment of the present invention, a barrier layer is provided within the catheter that is comprised of material which has a lower permeability than conventional materials used in the wall of a catheter. Thus, preferably, the barrier layer material has a lower permeability for molecules in the infusion formulation and in the environment of use than conventional materials used in the wall of a catheter. Thus, the properties, composition, and/or stability of the infusion formulation delivered to the infusion site may be more accurately controlled. In one preferred embodiment, the undesirable substance is believed to be $CO_2$ and the infusion formulation comprises an insulin formulation.

Preferred embodiments of the present invention also provide a catheter which inhibits deposit formation at the distal end tip and facilitates the expulsion during delivery of a bolus or catheter flush. According to one embodiment, a flared distal end tip aids in the release, during a bolus delivery or catheter flush, of any obstruction situated at the distal end tip of the catheter. The larger cross-sectional area of the inner channel of the lumen at the flared distal end tip minimizes the chances that any obstruction that develops at or near the distal end tip will be sufficient to hinder the flow of the infusion formulation within the lumen of the catheter. In addition, deposits that do form in the flared portion of the distal end tip are more likely to be expelled during a bolus delivery or catheter flush due to the shape and larger cross-sectional area of the flare.

Further preferred embodiments of the present invention also provide a catheter which inhibits deposit formation at or near the distal end tip by providing a slit valve that greatly reduces the potential for obstructions resulting from the mixing of body fluids with the infusion formulation during the interval between pump strokes of an infusion pump. The slit valve comprises a portion of the outer layer material extended over the distal end with one or more and, preferably a plurality of slits that may be elastically extended to an open position by the expulsion of the infusion formulation during a pump stroke of the infusion pump. During the interval between pump strokes, the slits will return to a closed position and hinder the inflow of body fluid into the distal end tip.

Further preferred embodiments of the present invention comprise a catheter which provides an annular channel to aid in the delivery of the infusion formulation to the infusion site in the event of an obstruction at or near the distal end tip of the catheter. This annular channel is formed in the layers of the catheter at a sufficient upstream distance from the distal end tip to provide an alternate passageway, under sufficient pressure, for the infusion formulation to flow to the infusion site through the annular channel.

Depending upon the context of use, the invention may include various combinations of these features which function together to provide protection against diffusion of substances through the catheter layers and against the formation of catheter obstructions. Various embodiments of the invention include one or more of these features. Preferred embodiments of the present invention contain each of these features.

These and other objects, features, and advantages of embodiments of the invention will be apparent to those skilled in the art from the following detailed description of embodiments of the invention, when read with the drawings and appended claims.

BRIEF DESCRIPTION OF THE DRAWINGS

Referring now to the drawings in which like reference numbers represent corresponding parts throughout.

DETAILED DESCRIPTION OF PREFERRED EMBODIMENTS

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the preferred embodiments of the present invention.

Figure 1:
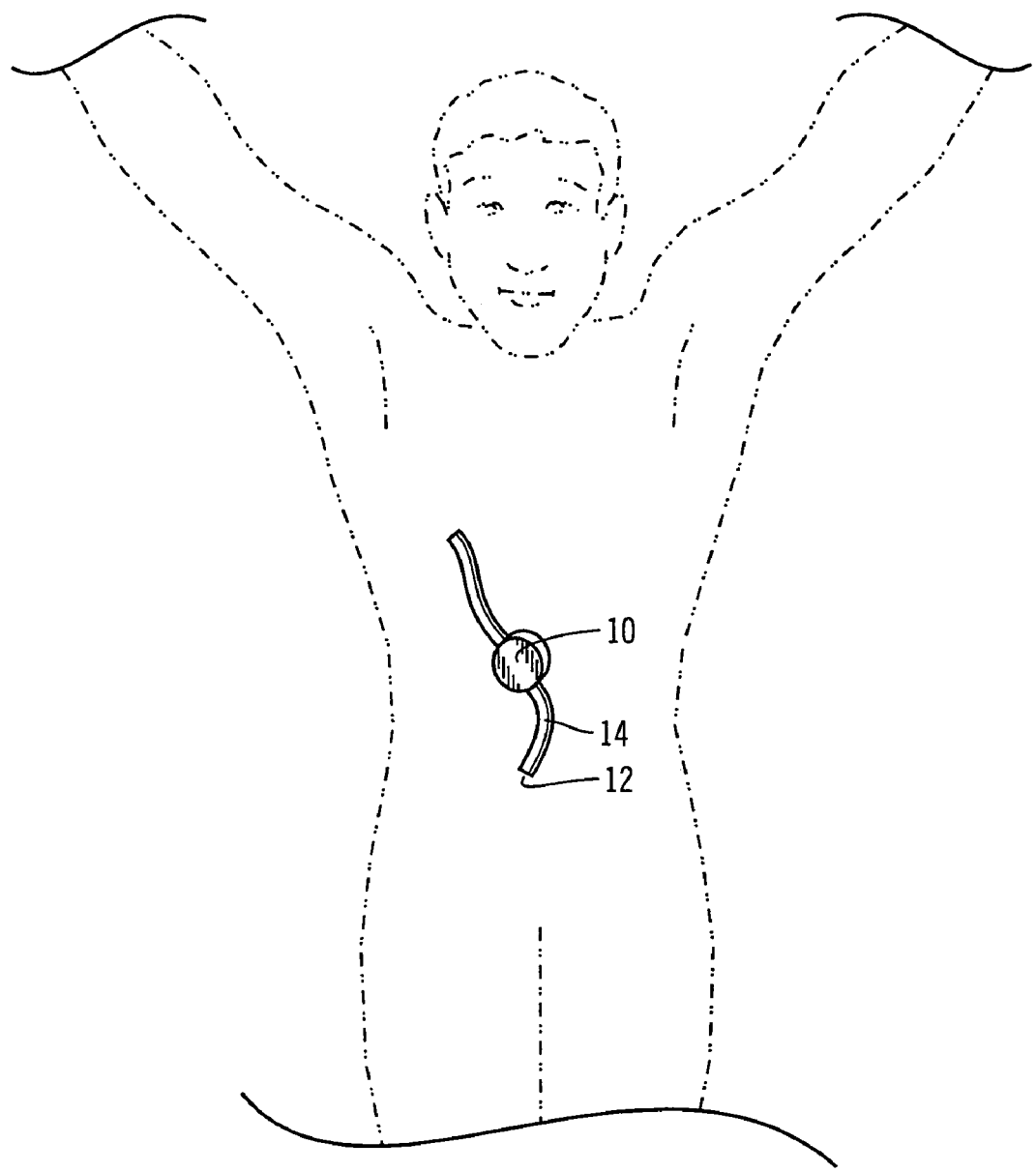
FIG. 1 shows a fragmented cutaway view of an exemplary environment of use of the present invention for the intraperitoneal delivery of an insulin formulation.

As discussed above, the present invention relates generally to an improved catheter. Embodiments of the invention may be employed in various infusion environments including, but not limited to a biological implant environment. In preferred embodiments, a catheter is configured for an implant environment within a human body, as shown in FIG. 1. However, other embodiments may be employed in other biological implant or non-implant environments.

Figure 2:
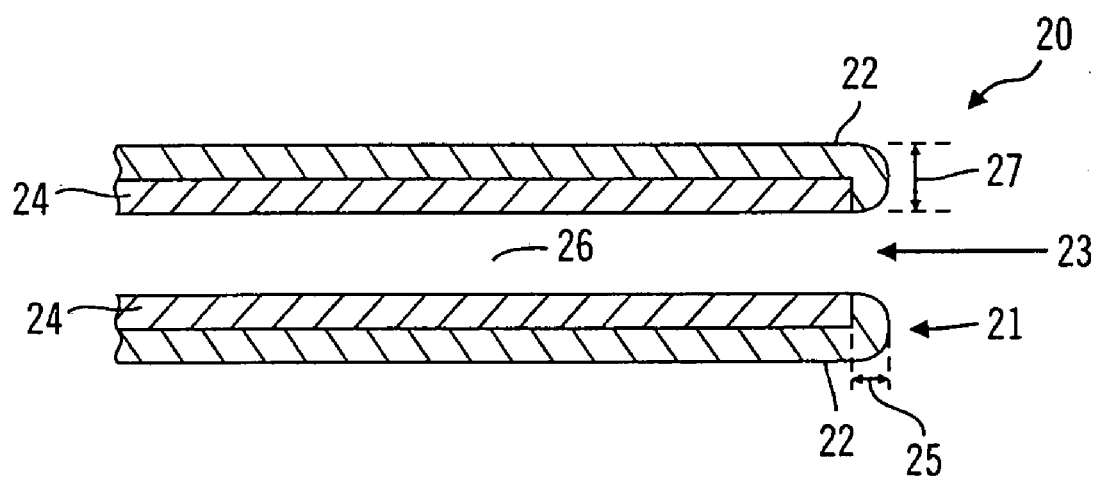
FIG. 2 illustrates a fragmented cutaway view of an example of a catheter with a barrier layer according to an embodiment of the invention.

FIG. 2 illustrates an example of a catheter 20 according to one preferred embodiment of the present invention. Catheter 20, shown in a fragmented cutaway view in FIG. 2, may be used in conjunction with an IIP. Catheter 20 comprises a lumen 26 which extends through a barrier layer 24 having a relative stiffness and density suitable for the environment of use. The material used for barrier layer 24 may be selected from the group of halogenated polymers such as, but not limited to, polytetrafluorethylene (PTFE Teflon), polyvinylidene chloride (Saran), polyvinylidene fluoride (Kynar), or derivatives of any of these materials. Other suitable materials include polymeric materials such as, but not limited to, polyamides, ethylene-vinyl alcohol (EVOH), polyetheretherketone (PEEK), nylon, polyester, or derivatives of any of these materials. In addition, inorganic materials such as, but not limited to, glass capillary tubing or diamond coated tubing may be used for the barrier layer 24. Catheter 20 also comprises an outer layer 22 of soft, flexible, bio-compatible material such as, but not limited to, relatively soft silicone rubber or polyethylene.

In a preferred embodiment of the present invention, the outer layer 22 is in firm contact with and substantially covers the barrier layer 24. The outer layer 22 protrudes beyond the barrier layer 24 at the distal end tip 23 a distance sufficient to cover the edge of the barrier layer 24, as referenced by numeral 21. The soft material of outer layer 22 preferably is formed to conform to and cover the edge of the barrier layer 24. This reduces irritation to the patient, as the barrier layer 24 may be relatively rigid and may irritate tissue with which the tip comes into direct contact.

Preferably, the length of the protrusion of the outer layer 22 beyond barrier layer 24 is selected to provide sufficient coverage of the edge of the barrier layer, but not so long as to allow significant diffusion into or out of the infusion formulation prior to the infusion formulation being discharged from the distal end tip 23. Obstructions at the distal end tip 23 may occur for at least three reasons. First, because the volume of the infusion formulation (such as an insulin formulation) situated in the distal end tip 23 has been present in the catheter the longest period of time, it has been subjected to any diffusion longer than the remainder of the infusion formulation present in the catheter. Second, the volume of the infusion formulation situated in the portion of the distal end tip 23 without the protection of barrier layer 24 will be more likely to encounter diffusing $CO_2$ and other substances. Third, stabilizers or preservatives may be lost by diffusion and/or interaction with materials that mix with the infusion formulation through the opening at the distal end tip 23. Therefore, the portion of the outer layer 22 that protrudes beyond the barrier layer 24 at the distal end tip 23 may provide an attachment site for obstructions due to lack of a barrier layer in that portion of the catheter 20. Accordingly, in some embodiments this portion may be kept to a minimum.

In a preferred embodiment of the present invention, in order to minimize the potential for obstructions, the distance that outer layer 22 protrudes beyond barrier layer 24 may surround a volume no greater than the smallest possible pump stroke volume of the IIP, i.e., the smallest possible amount of infusion formulation displaced per actuation of the IIP. This will result in a minimum exposure time for the infusion formulation in the unprotected portion of the distal end tip 23. In the alternative, the distance may be based on surrounding a volume no greater than a volume corresponding to a predefined number of pump strokes.

Alternatively, the distance that outer layer 22 protrudes beyond barrier layer 24 may fall within a possible range of distances. In embodiments of the present invention, a range of distances between one-half inch to one inch may be used. In a preferred embodiment, the distance for the protrusion of outer layer 22 beyond barrier layer 24 may be one-half inch. Similarly, the ratio of protrusion length to thickness for outer layer 22 may fall within a possible range. In embodiments of the present invention, a range of ratios between 0.5 and 50 may be used. More preferably, a range between 1 and 20 may be used. Most preferably, a range between 1 and 10 may be used. In a preferred embodiment of the present invention, the ratio of length to thickness of outer layer 22 may be one to one, i.e., the length of the protrusion beyond the distal end tip 23, referenced by numeral 25, may be equal to the thickness of the outer layer 22, referenced by numeral 27. Other embodiments may employ other dimensions and ratios.

In a preferred embodiment of the present invention, catheter 20 shown in FIG. 2 may be used to deliver Lispro or other forms of insulin formulation to the patient. It is believed that diffusion of $CO_2$ through the layers or up the distal end tip of the catheter leads to precipitation and eventually to the formation of deposits that may result in catheter obstructions. Thus, in prior art catheters, Lispro and other forms of insulin formulation may be susceptible to the formation of obstructions due to the insufficient barriers these catheters provided against diffusion of $CO_2$ and other substances. These obstructions result in destabilization of the Lispro, and the Lispro may be hindered in reaching the infusion site.

Preferred embodiments of the present invention significantly reduce the amount of diffusion through the catheter layers by providing a barrier layer for the catheter. In embodiments of the present invention, the barrier layer may be made of a material that is compatible with the environment of use (for example, infusion formulation compatible and, if necessary, bio-compatible and bio-stable). In a preferred embodiment of the present invention, the material of barrier layer 24 is PTFE Teflon and the undesirable substance is $CO_2$.

PTFE Teflon is chosen because it is insulin formulation compatible, bio-compatible, bio-stable, and has a gas permeability index for $CO_2$ that is much lower than that of other materials commonly used in a catheter wall. The gas permeability index, in reference to a specified material, indicates the ability of a specified gas to permeate through the material. For example, the gas permeability index of PTFE Teflon for $CO_2$ is 6.8 (cc-mm/sec-cm$^2$-cmHg). In contrast, the gas permeability index of polyethylene for $CO_2$ is 280 (cc-mm/sec-cm$^2$-cmHg). Thus, the use of PTFE Teflon as a $CO_2$ barrier can result in a barrier that is as much as 40 times more effective than polyethylene, assuming the same dimensions of the catheter. Thus, barrier layer 24 substantially hinders diffusion of $CO_2$ into the lumen of catheter 20.

An additional advantage to the use of PTFE Teflon in a catheter is its relative stiffness. This stiffness may facilitate the projection of the catheter through the body. For example, in the intraperitoneal delivery of insulin formulation discussed above, the catheter is projected through the peritoneal wall of a patient. The added stiffness provided by the PTFE Teflon may be beneficial for such uses of the catheter.

Figure 3:
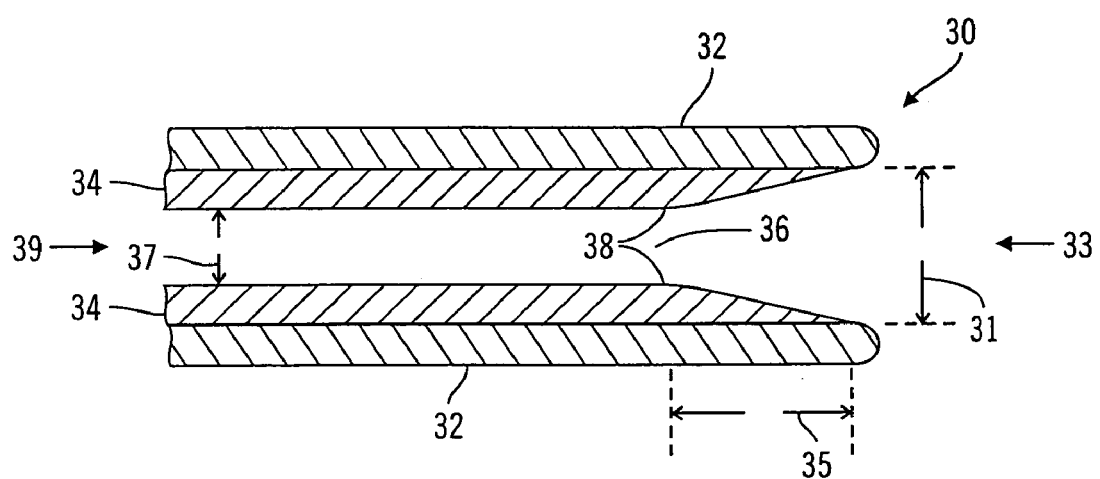
FIG. 3 illustrates an example of a catheter with a flared distal end tip according to an embodiment of the invention.

A further preferred embodiment of the present invention has a flared or tapered distal end tip to aid in the release, during a bolus delivery or catheter flush, of any deposited precipitated substance situated at or near the distal end tip of the catheter. FIG. 3 shows a fragmented cutaway view of catheter 30. Catheter 30 comprises a lumen 36 which extends through a barrier layer 34 of relatively stiff, dense material. The material used for barrier layer 34 may be selected from the group of halogenated polymers such as, but not limited to, PTFE Teflon, Saran, Kynar, or derivatives of any of these materials. Other suitable materials include polymeric materials such as, but not limited to, polyamides, EVOH, PEEK, nylon, polyester, or derivatives of any of these materials. In addition, inorganic materials such as, but not limited to, glass capillary tubing or diamond coated tubing may be used for the barrier layer 34. Catheter 30 further comprises an outer layer 32 of soft, flexible, bio-compatible material such as, but not limited to, relatively soft silicone rubber or polyethylene.

In a preferred embodiment of the present invention, the outer layer 32 is in firm contact with and substantially covers the barrier layer 34. The outer layer 32 protrudes beyond the barrier layer 34 at the distal end tip 33 of catheter 30 a distance sufficient to cover the edge of the barrier layer 34. As discussed above in reference to FIG. 2, the soft material of outer layer 32 preferably is formed to conform to and cover the edge of the barrier layer 34.

Beginning at a specified distance from the distal end tip 33, referred to in the present application as the "apex" 38, the inner cross-sectional diameter of the lumen 36, bounded by barrier layer 34, becomes progressively larger as it extends toward the distal end tip 33. This results in the flaring of the lumen 36 as it extends from the apex 38 towards the distal end tip 33. The inner cross-sectional diameter of the lumen 36 increases but, in preferred embodiments, the outer cross-sectional diameter of the lumen 36 remains relatively constant. Thus, it is easier to pass catheter 30 through small incisions and irritation is reduced.

In embodiments of the present invention, the cross-sectional diameter of the portion of the lumen 36 that extends from the apex 38 towards the proximal end 39, i.e., the unflared portion of the lumen 36, may be about 0.007 inch. In a preferred embodiment of the present invention the distance of apex 38 from distal end tip 33 may be approximately 0.5 inch. The lumen 36-will continue to flare as it progresses to the distal end tip 33. In embodiments of the present invention, the cross-sectional diameter of the lumen 36 at its widest point, i.e., at the distal end tip 33, may be about 0.020 inch. Other embodiments may employ other dimensions.

The larger cross-sectional area at the distal end tip 33 minimizes the chances that any obstruction that develops at or near the distal end tip 33 will be sufficient to hinder the flow of the infusion formulation within the lumen 36. In addition, deposits that do form in the flared portion of distal end tip 33 are more likely to be expelled during a bolus delivery or catheter flush due to the shape and larger cross-sectional area of the flare. Other shapes besides a flare shape for the distal end tip 33 are also possible. For example, the transition to a larger cross-sectional area of the inner surface of the lumen 36 may take place more abruptly with a more uniformly cylindrical shape for the widened portion of lumen 36 nearest the distal end tip 33.

The flared or tapered shape of the distal end tip 33 has another advantage. During the interval between IIP pump strokes, body fluids will mix with the infusion formulation present at the distal end tip 33. The area of the lumen 36 into which the body fluids will penetrate is referred to as the "mixing zone." The potential for the formation of obstructions in the mixing zone is high due to the mixing of substances within the body fluids with substances within the insulin formulation.

The flared or tapered distal end tip 33 of the embodiment of the present invention illustrated in FIG. 3 greatly reduces the potential for complete obstructions by selecting the distance of the apex 38 from the distal end tip 33 such that the mixing zone of the lumen 36 is contained within the flare. Because the mixing zone is contained within the larger diameter of the flare and not within the smaller diameter of the remainder of the lumen 36, the potential for complete obstructions resulting from the mixing of body fluids with the insulin formulation is greatly reduced.

Figure 4:
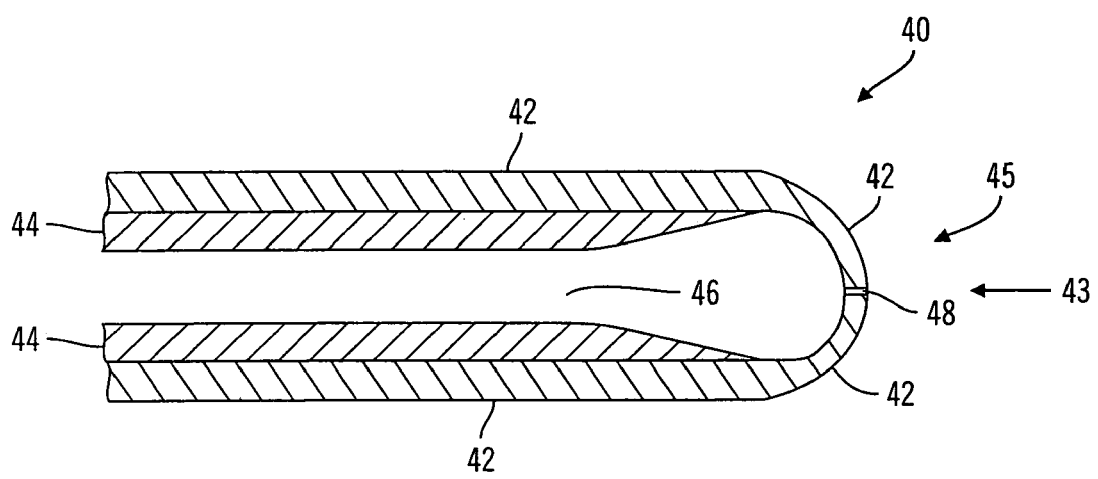
FIG. 4 illustrates a fragmented cutaway view of an example of a catheter with a slit valve at the distal end tip according to an embodiment of the invention.

Another preferred embodiment of the present invention further reduces potential for obstructions in the mixing zone by providing a slit valve to cover the distal end tip of the catheter to prevent body fluids from entering the mixing zone during the interval between IIP pump strokes. FIG. 4 shows a fragmented cutaway view of catheter 40. Catheter 40 comprises a lumen 46 which extends through a barrier layer 44 of relatively stiff, dense material. The material used for barrier layer 44 may be selected from the group of halogenated polymers such as, but not limited to, PTFE Teflon, Saran, Kynar, or derivatives of any of these materials. Other suitable materials include polymeric materials such as, but not limited to, polyamides, EVOH, PEEK, nylon, polyester, or derivatives of any of these materials. In addition, inorganic materials such as, but not limited to, glass capillary tubing or diamond coated tubing may be used for the barrier layer 44. Catheter 40 further comprises an outer layer 42 of soft, flexible, bio-compatible material such as, but not limited to, relatively soft silicone rubber or polyethylene.

In a preferred embodiment of the present invention, the outer layer 42 is in firm contact with and substantially covers the barrier layer 44. The outer layer 42 protrudes beyond the barrier layer 44 at the distal end tip 43 a sufficient amount to form slit valve 45. Slit valve 45 has a semi-spherical shape. Other shapes are also possible. For example, slit valve 45 could have a conical shape with the cross-sectional area gradually narrowing from the distal end tip 43 outward. Slit valve 45 has a slit 48 that may be elastically extended to an open position by the expulsion of the infusion formulation during an IIP pump stroke. During the interval between IIP pump strokes, the slit 48 will elastically return to a closed position and hinder the inflow of body fluids. Thus, slit valve 45 greatly reduces the potential for the formation of obstructions resulting from the mixing of body fluids with the infusion formulation during the interval between IIP pump strokes.

In other preferred embodiments, slit valve 45 may comprise one or more and, preferably a plurality of slits. Also, the slits may be positioned at various points on the slit valve, for example, along the sides of the slit valve. Further, the slit valve may also be utilized in a non-flared catheter such as the catheter discussed above in relation to FIG. 2.

Figure 5:
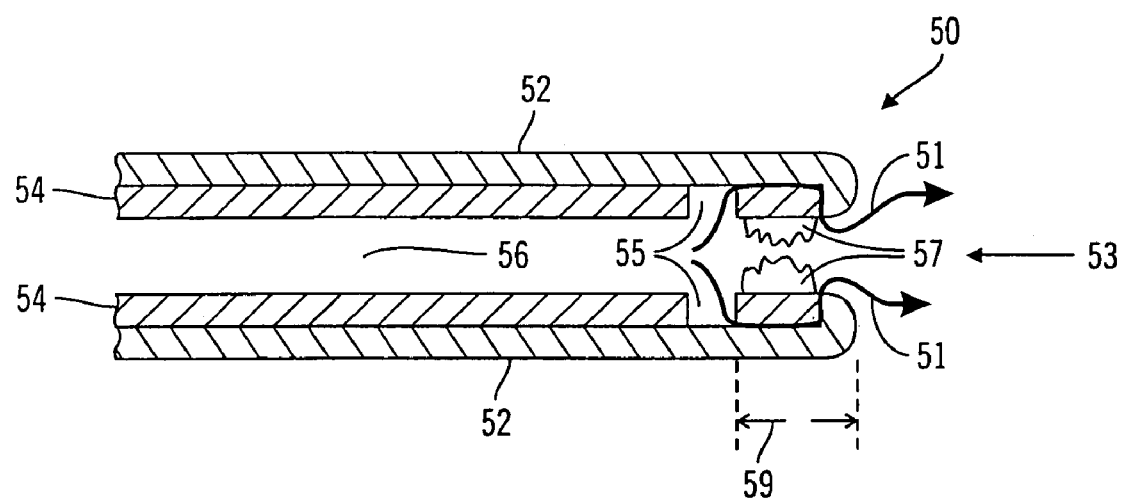
FIG. 5 illustrates a fragmented cutaway view of an example of a catheter with an annular channel according to an embodiment of the invention.

A further preferred embodiment of the present invention provides alternate paths for the flow of the infusion formulation out of the distal end tip in the event that the tip becomes blocked. FIG. 5 shows a fragmented cutaway view of catheter 50. Catheter 50 comprises a lumen 56 which extends through a barrier layer 54 of relatively stiff, dense material. The material used for barrier layer 54 may be selected from the group of halogenated polymers such as, but not limited to, PTFE Teflon, Saran, Kynar, or derivatives of any of these materials. Other suitable materials include polymeric materials such as, but not limited to, polyamides, EVOH, PEEK, nylon, polyester, or derivatives of any of these materials. In addition, inorganic materials such as, but not limited to, glass capillary tubing or diamond coated tubing may be used for the barrier layer 54. Catheter 50 also comprises an outer layer 52 of soft, flexible, bio-compatible material such as, but not limited to, relatively soft silicone rubber or polyethylene.

In a preferred embodiment of the present invention, the outer layer 52 is in firm contact with and substantially covers the barrier layer 54. The outer layer 52 protrudes beyond the barrier layer 54 at the distal end tip 53 a distance sufficient to cover the edge of the barrier layer 54. The soft material of outer layer 52 preferably is formed to conform to and cover the edge of the barrier layer 54. Flowholes 55 are formed in barrier layer 54 to allow the infusion formulation to flow through an annular channel 58, the entrance into which is formed between the outer surface of barrier layer 54 and the inner surface of outer layer 52 at a specified distance, referred to by numeral 59, from the distal end tip 53. The distance is chosen such that the entrance into the annular channel 58 will be sufficiently upstream from the mixing zone and, thus, from any obstruction. In a preferred embodiment of the present invention, distance 59 is approximately 0.50 inch from the distal end tip 53. Other embodiments may employ other distances.

If an obstruction 57 forms at the distal end tip 53, the pressure of the outward flow of the infusion formulation during an IIP pump stroke will be sufficient to elastically separate the outer surface of the barrier layer 54 from the inner surface of the outer layer 52 along the annular channel 58, providing a passageway for the infusion formulation. Thus, the infusion formulation will flow around the obstruction 57 and to the infusion site, as shown by directed arrows 51. In the interval between IIP pump strokes, the outer surface of the barrier layer 54 will elastically return to contact the inner surface of the outer layer 52 along the annular channel 58.

Figure 6:
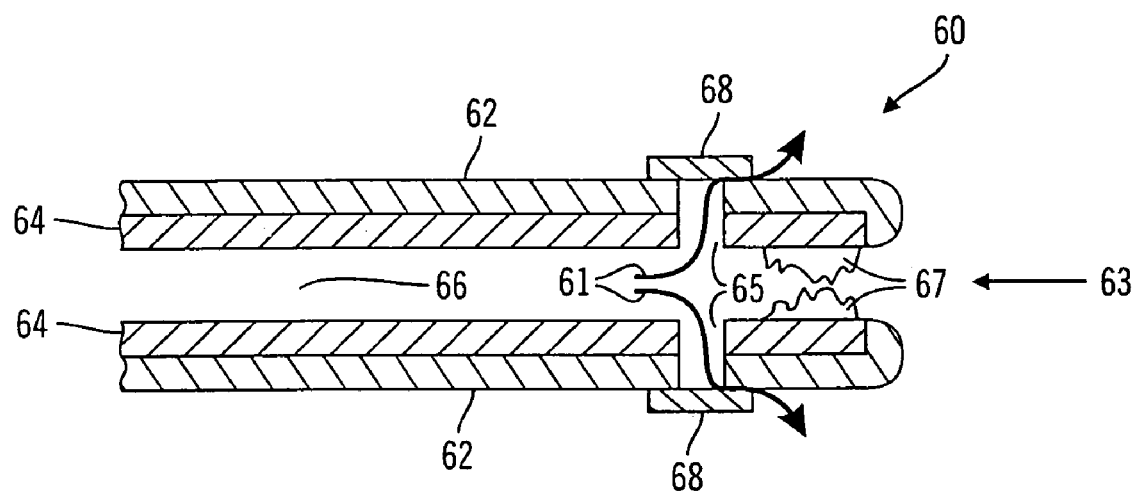
FIG. 6 illustrates a fragmented cutaway view of an example of a catheter with an annular channel and annular plug according to an embodiment of the invention.

An example of an alternative preferred embodiment of the present invention is shown in FIG. 6. FIG. 6 shows catheter

60. Catheter 60 comprises a lumen 66 which extends through a barrier layer 64 of relatively stiff, dense material. The material used for barrier layer 64 may be selected from the group of halogenated polymers such as, but not limited to, PTFE Teflon, Saran, Kynar, or derivatives of any of these materials. Other suitable materials include polymeric materials such as, but not limited to, polyamides, EVOH, PEEK, nylon, polyester, or derivatives of any of these materials. In addition, inorganic materials such as, but not limited to, glass capillary tubing or a diamond coated tubing may be used for the barrier layer 64. Catheter 60 also comprises an outer layer 62 of soft, flexible, bio-compatible material such as, but not limited to, relatively soft silicone rubber or polyethylene.

In a preferred embodiment of the present invention, the outer layer 62 is in firm contact with and substantially covers the barrier layer 64. The outer layer 62 protrudes beyond the barrier layer 64 at the distal end tip 63 a distance sufficient to cover the edge of the barrier layer 64. The soft material of outer layer 62 preferably is formed to conform to and cover the edge of the barrier layer 64.

Flowholes 65 are formed in barrier layer 64 and outer layer 62 to allow the infusion formulation to flow through an annular channel 69, the entrance into which is formed between annular plug 68 and the outer surface of outer layer 62. Annular plug 68 is disposed over flowholes 65. Annular plug 68 may be a soft, flexible, bio-compatible material such as, but not limited to, relatively soft silicone rubber or polyethylene. Annular plug 68 provides an adequate seal against outflow through flowholes 65 of the infusion formulation within lumen 66 under normal pressure. However, if an obstruction, referred to by numeral 67, develops at or near the distal end tip 63, then the pressure of the outward flow of the infusion formulation during an IIP pump stroke will be sufficient to elastically separate the inner surface of the annular plug 68 from the outer surface of the outer layer 62, providing a passageway for the infusion formulation through annular channel 69. Thus, the infusion formulation will flow around the obstruction 67 and to the infusion site, as shown by directed arrows 61. During the interval between IIP pump strokes, the inner surface of the annular plug 68 will elastically return to the outer surface of the outer layer 62.

Figure 7:
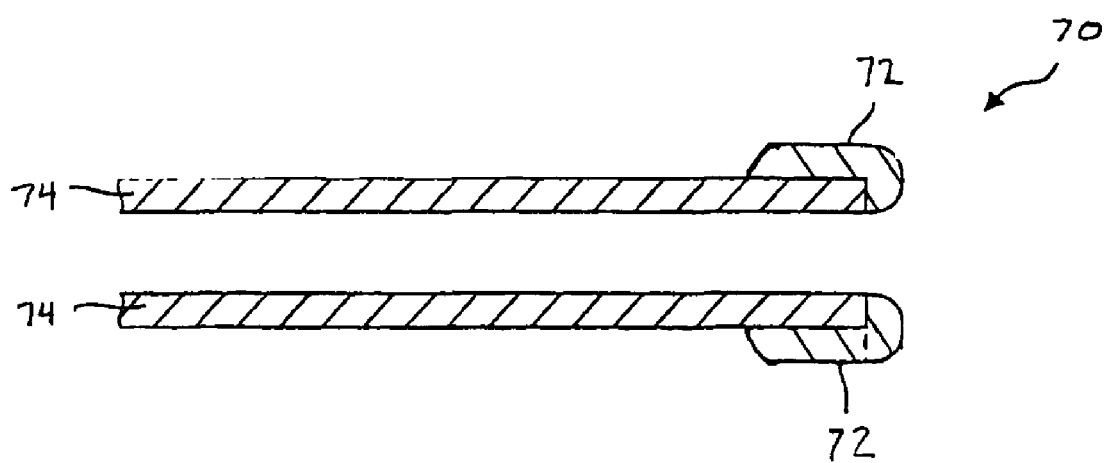
FIG. 7 illustrates a fragmented cutaway view of an example of a catheter with an outer layer at the distal end of the catheter.

FIG. 7 shows a catheter 70 having an inner surface of the outer layer 72 which covers the outer surface of the barrier layer 74 only at the distal end of the catheter.

In all of the preferred embodiments of the present invention discussed above, an additional interior layer may be provided on the inner surface of the barrier layer. The material provided for the interior layer may be hydrophobic or hydrophilic in nature in order to regulate the interaction of infusion formulation components with the interior surface. The interior catheter surface may also contain or be treated to contain chemical groups that permit the covalent or physical attachment of compounds that will regulate its surface properties and permeability.

Further, in preferred embodiments of the present invention the barrier layer may be sandwiched between layers of bio-compatible material such as, but not limited to, polyethylene and silicone rubber. Thus, the barrier layer will continue to provide a barrier against diffusion of substances into or out of the catheter. In some applications, the barrier layer may be the outermost layer of the catheter.

Furthermore, in some applications, it may be determined that the advantages of the invention's barrier layer described above are only required in a portion of the catheter. Thus, in some embodiments of the invention's catheter the barrier layer is used in only that portion of the catheter where the described advantages are most needed. In these embodiments, the remainder of the catheter may not comprise any barrier layer material.

In yet other applications, it may be advantageous to cover only a portion of the barrier layer material with the outer layer material. Thus, in some embodiments, the outer layer material covers only those portions of the barrier layer material where the advantages of the outer layer material (for example, softness and/or flexibility) are most needed, for example, at the distal end tip.

Catheter structures in accordance with various embodiments of the invention may be manufactured in any suitable manner, including, but not limited to, extruding or molding inner and outer layers together or separately.

Therefore, embodiments of the present invention provide a catheter which provides a significant barrier to diffusion of $CO_2$ and other substances into the lumen of the catheter. A barrier layer is provided as part of the catheter which inhibits the outward diffusion of substances flowing through the lumen of the catheter. Thus, the properties, composition, and/or stability of the infusion formulation delivered to the infusion site may be more accurately controlled.

Embodiments of the present invention also provide a catheter which inhibits deposit formation at the distal end tip and facilitates the expulsion during delivery, for example, delivery of a bolus or catheter flush The larger cross-sectional area of the flare at the distal end tip aids in the release, during a bolus delivery or catheter flush, of deposited precipitated substances situated at the distal end tip of the catheter and minimizes the chances that any obstruction that develops at the distal end tip will be sufficient to hinder the flow of the infusion formulation within the lumen of the catheter to the infusion site.

Embodiments of the present invention also provide a catheter which inhibits deposit formation at the distal end tip by providing a slit valve at the distal end tip. The slit valve has one or more and, preferably a plurality of slits that may be elastically extended to an open position by the expulsion of the infusion formulation during an IIP pump stroke. During the interval between IIP pump strokes, the slits will return to a closed position and hinder the inflow of body fluid into the distal end tip.

Embodiments of the present invention also provide a catheter which provides an annular channel. This annular channel may be formed in the catheter at a sufficient upstream distance from the distal end tip to provide an alternate passageway for the infusion formulation to the infusion site through the annular channel in the event of an obstruction.

Thus, embodiments of the present invention provide a catheter which inhibits diffusion of substances through the layers of the catheter and which minimizes the chances that the flow of infusion formulations through the catheter will be blocked.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A catheter for use in conveyance of a formulation, the catheter comprising:
   an outer material;
   an inner barrier material;
   a proximal end; and
   a distal end;
   wherein the inner barrier material at the distal end forms an innermost surface around a fluid flow passage of the catheter, where the innermost surface of the inner barrier material flares outward to widen the fluid flow passage adjacent the distal end of the catheter; and
   wherein the outer material protrudes a distance beyond the inner barrier material at the distal end and forms a generally semi spherical segment spaced from and enclosing the distal end, the semi spherical segment comprising at least one slit formed thereon, the at least one slit expanding upon a pump stroke of an infusion pump to release the formulation and closing at an interval between pump strokes to hinder inflow of substances into the distal end of the catheter.

2. The catheter as recited in claim 1, wherein the outer material has a dimension relative to the inner barrier material such that the outer material is in firm contact with the inner barrier material.

3. The catheter as recited in claim 2, wherein the outer material is held in a fixed in position relative to the inner barrier material.

4. The catheter as recited in claim 2, wherein the outer material has a longitudinal length dimension and wherein the inner barrier material remains stationary relative to the longitudinal length dimension of the outer material.

5. The catheter as recited in claim 1, wherein the outer material has an inner surface and the inner barrier material has an outer surface, the inner surface of the outer material substantially covers the outer surface of the inner barrier material.

6. The catheter as recited in claim 1, wherein the innermost surface of the inner barrier material has a substantially constant cross-sectional diameter along a length of the catheter between the proximal end and a location at which the inner barrier material flares outward to widen the fluid flow passage.

7. The catheter as recited in claim 6, wherein an outer diameter of the catheter at the distal end is substantially constant along a length of the catheter at which the inner barrier material flares outward to widen the fluid flow passage.

8. The catheter as recited in claim 1, further comprising an occlusion zone having a length extending along a portion of a length of the catheter from the distal end of the catheter toward the proximal end of the catheter, the innermost surface of the inner barrier material flaring outward to widen the fluid flow passage along the entire length of the occlusion zone.

9. The catheter as recited in claim 8, wherein an outer diameter of the catheter at the distal end is substantially constant along the entire length of the occlusion zone.

10. The catheter as recited in claim 8, wherein an outer diameter of the catheter is substantially constant along a length of the occlusion zone and along a further portion of the length of the catheter extending from the occlusion zone toward the proximal end of the catheter.

11. The catheter as recited in claim 10, wherein an outer diameter of the catheter is substantially constant along the entire length of the occlusion zone.

12. The catheter as recited in claim 1, further comprising an occlusion zone having a length extending along a portion of a length of the catheter from the distal end of the catheter toward the proximal end of the catheter, the inner surface of the barrier layer flaring outward to widen the fluid flow passage along the entire length of the occlusion zone, wherein an outer diameter of the catheter at the distal end is substantially constant along the entire length of the occlusion zone.

13. The catheter as recited in claim 1, wherein the outer material is held in a fixed in position relative to the inner barrier material.

14. The catheter as recited in claim 1, wherein the outer material has a longitudinal length dimension and wherein the inner barrier material remains stationary relative to the longitudinal length dimension of the outer material.

15. An implantable infusion pump system, for use in delivery of a formulation, the system comprising:
a pump for delivering measured doses of a formulation;
a sensing device for regulating the delivery of the formulation; and
a catheter for conveying the formulation from the pump to an infusion site, the catheter comprising:
an outer layer comprising an outer surface and an inner surface;
a barrier layer comprising an outer surface and an inner surface;
a proximal end; and
a distal end having a surface on which an obstruction may form;
wherein the inner surface of the barrier layer borders all sides of a fluid flow channel at the distal end of the catheter for the formulation and flares outward to widen the fluid flow passage adjacent the distal end of the catheter;
wherein the outer layer protrudes a distance beyond the barrier layer at the distal end and forms a generally semi spherical segment spaced from and enclosing the distal end, the semi spherical segment comprising at least one slit formed thereon, the at least one slit expanding upon a pump stroke of an infusion pump to release the formulation and closing at an interval between pump strokes to hinder inflow of substances into the distal end of the catheter.

16. The system as recited in claim 15, wherein the outer layer has a dimension relative to the barrier layer such that the outer layer is in firm contact with the barrier layer.

17. The system as recited in claim 15, further comprising an occlusion zone having a length extending along a portion of a length of the catheter from the distal end of the catheter toward the proximal end of the catheter, the inner surface of the barrier layer flaring outward to widen the fluid flow passage along the entire length of the occlusion zone.

18. The system as recited in claim 17, wherein an outer diameter of the catheter at the distal end is substantially constant along the entire length of the occlusion zone.

19. The system as recited in claim 17, wherein an outer diameter of the catheter is substantially constant along a length of the occlusion zone and along a further portion of the length of the catheter extending from the occlusion zone toward the proximal end of the catheter.

20. The system as recited in claim 19, wherein an outer diameter of the catheter is substantially constant along the entire length of the occlusion zone.

21. A catheter, for use in delivery of a formulation, the catheter comprising:
an outer layer comprising an outer surface and an inner surface;
a barrier layer comprising an outer surface and an inner surface;
a proximal end; and
a distal end;
wherein the inner surface of the outer layer covers the outer surface of the barrier layer at the distal end of the catheter and wherein the inner surface of the barrier layer borders all sides of a fluid flow passage at the distal end of the catheter and flares outward to widen the fluid flow passage adjacent the distal end of the catheter; and
wherein the outer layer protrudes a distance beyond the barrier layer at the distal end and forms a generally semi spherical segment spaced from and enclosing the distal end, the semi spherical segment comprising at least one slit formed thereon, the at least one slit expanding upon a pump stroke of an infusion pump to release the formulation and closing at an interval between pump strokes to hinder inflow of substances into the distal end of the catheter.

* * * * *